United States Patent [19]

Szita et al.

[11] Patent Number: 5,294,671
[45] Date of Patent: Mar. 15, 1994

[54] MONOMERIC AMINOPLAST CROSSLINKING AGENTS

[75] Inventors: Jeno G. Szita, Norwalk; Robert G. Lees, Stamford, both of Conn.

[73] Assignee: American Cyanamid Company, Stamford, Conn.

[21] Appl. No.: 60,135

[22] Filed: May 13, 1993

[51] Int. Cl.$^5$ ............................................. C08G 12/32
[52] U.S. Cl. ...................................... 525/187; 525/190; 525/327.3; 525/329.9; 525/330.5; 525/331.9; 525/375; 525/443; 525/455; 528/59; 528/73; 528/232; 528/259; 427/385.5; 427/386; 428/411.1; 428/413; 428/423.1
[58] Field of Search ................. 525/187, 190, 327.3, 525/329.9, 330.5, 331.9, 375, 443, 455; 528/59, 73, 232, 259, 261; 427/385.5, 386; 428/411.1, 413, 423.1; 544/197

[56] References Cited

U.S. PATENT DOCUMENTS

| | | | |
|---|---|---|---|
| 3,290,50 | 12/1966 | Hoover | 260/453 |
| 4,130,577 | 12/1978 | Nagato et al. | 260/453 |
| 4,377,530 | 3/1983 | Trenbeath et al. | 260/453 |
| 4,439,616 | 3/1984 | Singh et al. | 560/25 |
| 5,071,938 | 12/1991 | Halpaap et al. | 528/45 |

OTHER PUBLICATIONS

Abstract of German Patent No. 4,120,323, published Dec. 12, 1992.

*Primary Examiner*—Maurice J. Welsh
*Attorney, Agent, or Firm*—Bart E. Lerman; Michael J. Kelly; Claire M. Schultz

[57] ABSTRACT

A monomeric alkoxymethylated aminoplast crosslinking agent derived from a m-TMI/melamine 1:1 adduct and a process for its preparation is provided. The process comprises contacting melamine with M-TMI, contacting the adduct formed with formaldehyde, and contacting the hydroxymethylated adduct with an alcohol such as butanol. A curable composition comprising the monomeric aminoplast crosslinker and a polyfunctional active hydrogen-containing material is also provided. An improved method of coating using the curable composition to produce cured films or objects is also provided.

36 Claims, No Drawings

MONOMERIC AMINOPLAST CROSSLINKING AGENTS

BACKGROUND OF THE INVENTION

1. Field of the Invention

This invention relates to the preparation and use of a novel class of substantially monomeric aminoplasts as crosslinking agents. The crosslinkers are prepared from 2,4,6-triamino-1,3,5-triazine, hereinafter "melamine", and isopropenyl-alpha, alpha-dimethylbenzyl isocyanate, hereinafter "TMI", by a monoaddition reaction followed by methylolation and etherification.

2. Description of the Related Art

To effectively crosslink with a variety of widely available difunctional materials such as diols, dicarboxylic acids, dimercaptans, and diamides, a monomeric crosslinking agent is required to have a functionality effective for crosslinking of at least two. In many cases, however, even trifunctional aminoplast crosslinking agents do not give rise to sufficient crosslinking density in cured films or objects due to incomplete reaction of the functional groups, and as a result, cured films with inferior physical and resistance properties are obtained.

The problem of insufficient crosslinking density may be overcome by using a higher functional aminoplast crosslinker such as hexamethoxymethyl melamine. In these cases, however, the films obtained sometimes have low flexibility due to the somewhat rigid network produced in the films upon cure.

The above-identified problems of insufficient crosslinking of the low functionality crosslinkers and the low flexibility of the highly functional crosslinkers are both overcome by using typically tetrafunctional guanamine-derived aminoplast crosslinking agents. However, guanamine-derived crosslinkers are more difficult and more costly to prepare than melamine-derived crosslinkers. Furthermore, some guanamine crosslinkers such as N,N,N',N'-tetraalkoxymethylbenzoguanamines have insufficient resistance properties and have inferior stability towards the degradative action of ultraviolet light.

It is the object of this invention to obtain melamine-derived, substantially monomeric aminoplast crosslinking agents having olefinic functionality which are capable of producing, upon cure, films which have good acid resistance properties, environmental etch resistance, and a good balance of hardness and flexibility.

SUMMARY OF THE INVENTION

This invention relates to a novel, highly functional substantially monomeric aminoplast crosslinking agent and an intermediate used in the production thereof.

This invention also relates to a process for preparing said crosslinking agent.

This invention also relates to a curable composition containing said highly functional substantially monomeric aminoplast crosslinking agent.

This invention also relates to an improved method of coating using the curable composition of the invention.

Finally, this invention relates to a cured film or object prepared by the improved method of the invention.

DETAILED DESCRIPTION

This invention relates to meta-, para-, or a mixture of meta- and para-isopropenyl-alpha, alpha-dimethylbenzyl isocyanate adducts represented by the formula:

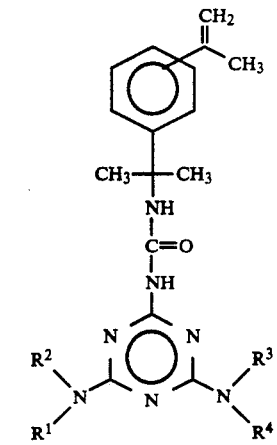

wherein each of $R^1$, $R^2$, $R^3$, and $R^4$ is independently selected from the group consisting of hydrogen, hydroxymethyl, an alkoxymethyl, an aminoplast-containing group derived from condensation thereof, and mixtures of any of the preceding groups.

The preferred isomer of the aminoplast is the metaisomer having at least one of the $R^1$, $R^2$, $R^3$, and $R^4$ groups selected independently from the group consisting of hydroxymethyl, alkoxymethyl of 1 to 6 carbon atoms, and mixtures thereof.

The most preferred aminoplasts are compositions of matter represented by the formula:

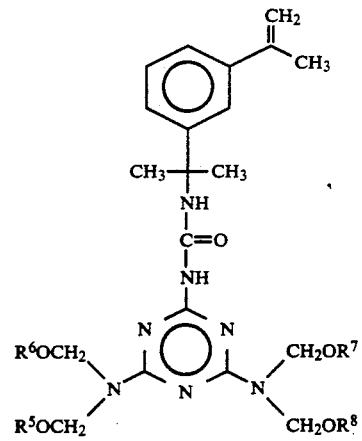

wherein each of $R^5$, $R^6$, $R^7$, and $R^8$ is independently selected from the group consisting of hydrogen, methyl, ethyl, 1-propyl, 2-propyl, 1-butyl, 2-butyl, iso-butyl, 1-pentyl, 1-hexyl and cyclohexyl groups, and mixtures thereof.

An example of the aminoplasts containing mixed alkoxy crosslinkably reactive groups is the particularly preferred composition of matter represented by the formula:

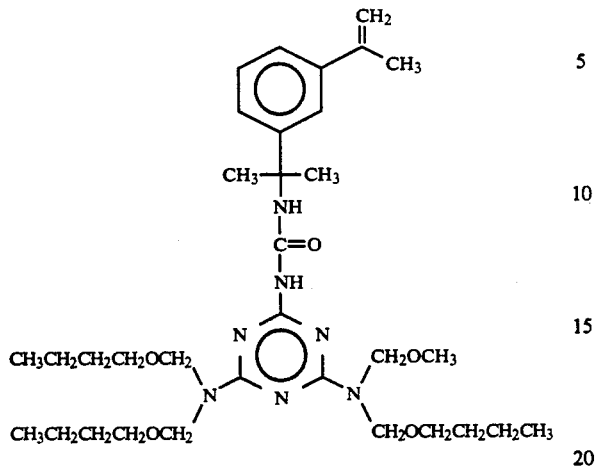

wherein the ratio of normal butyl to methyl groups is 3:1.

Preparation Of The Crosslinkers

The novel, substantially monomeric aminoplast crosslinking agents of the invention are prepared by a process in which a 1:1 adduct of melamine with an isocyanate is chemically modified to contain hydroxymethyl, alkoxymethyl or both groups. The isocyanate which forms the adduct is meta-isopropenyl alpha, alpha-dimethylbenzyl isocyanate (hereinafter m-TMI), available as TMI ® (meta) Unsaturated Aliphatic Isocyanate, a product of American Cyanamid Company, Wayne, N.J., or para-isopropenyl-alpha, alpha-dimethyl-benzyl isocyanate (hereinafter p-TMI), or a mixture of the meta- and para- isomers. The para-isomer may be prepared by procedures described in U.S. Pat. Nos. 3,290,350; 4,130,577; 4,377,530; or 4,439,616.

The reaction steps for preparing the novel tetrafunctional crosslinkers are illustrated below for the meta-isomer:

STEP (a)

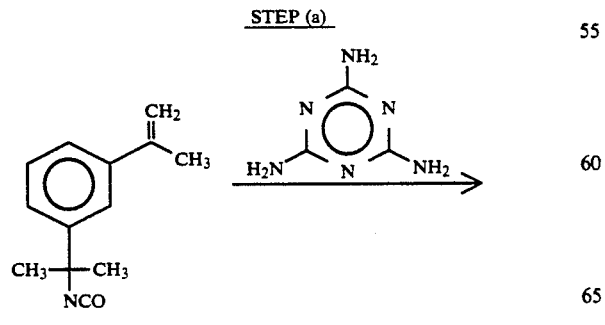

-continued

STEP (a)

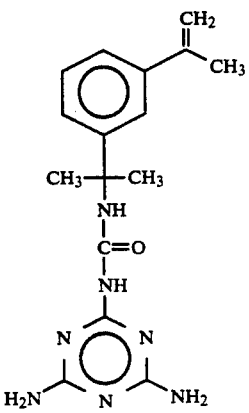

STEP (b)

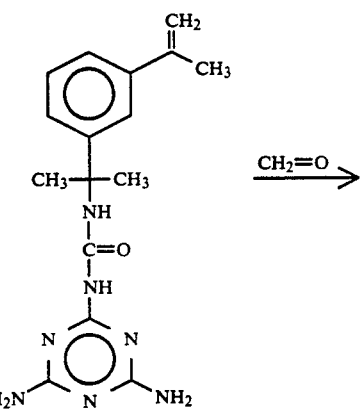

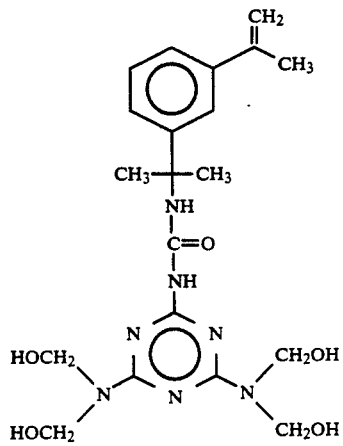

STEP (c)

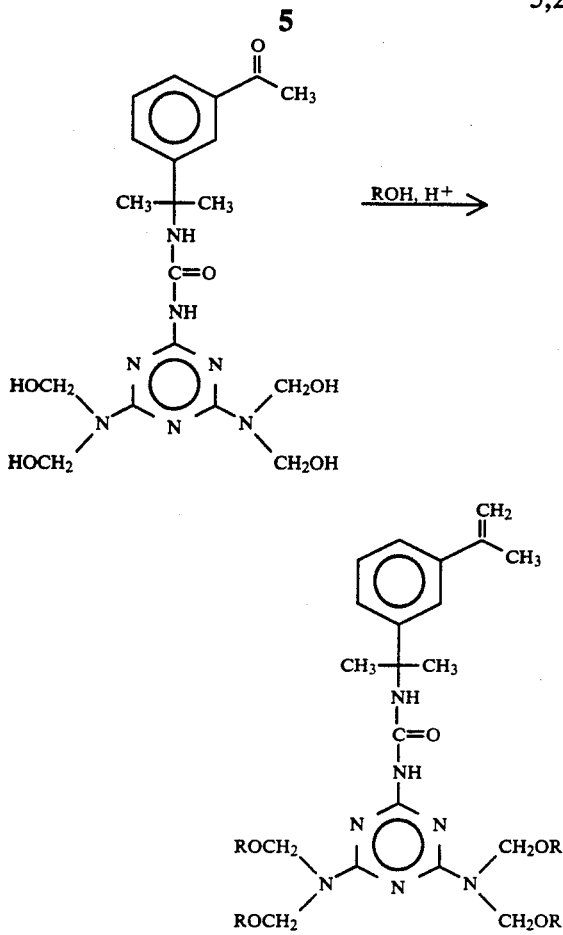

The novel process for preparing the aminoplast of the invention comprises:

(a) contacting melamine with isopropenyl-alpha, alpha-dimethylbenzyl isocyanate in a solvent characterized by a high dielectric constant, at a temperature and for a length of time sufficient to produce a 1:1 adduct, (b) contacting said 1:1 adduct of step (a) with 2 to 20 moles of formaldehyde per mole of adduct to produce a hydroxymethylated adduct, and (c) contacting said hydroxymethylated adduct of step (b) with 2 to 30 moles of an alcohol per mole of hydroxy-methylated adduct at an acidic pH to produce an alkoxymethylated aminoplast.

In step (a), the monoadduct of TMI and melamine is prepared using a 1:1 molar ratio of TMI to melamine, normally preferred on the basis of reaction stoicheometry. However, the adduct-forming reaction may be carried out at any ratio. For example, if a TMI to melamine molar ratio of 0.5:1 is used, there will remain a large excess of unreacted melamine which may be separated from the product, which product is necessarily a 1:1 adduct. If, on the other hand, excess quantities of TMI such as a 5:1 molar excess are used, only the monoaddition product is obtained under the process conditions of this invention. The unreacted TMI in this case may be easily removed by precipitation of the product.

The preferred solvents in step (a) are aprotic solvents having relatively high boiling points, high dipole moments and high dielectric constants for facilitating the dissolution of the sparingly soluble melamine at the reaction temperature and for allowing the product to crystallize at ambient temperatures. The preferred solvent is dimethylsulfoxide, however, aprotic solvents such as N,N-dimethylformamide, N,N-dimethylacetamide, N-methyl pyrrolidone, sulfolane, hexamethylphosphorus triamide (HMPT), hexamethylphosphoramide (HMPA), and mixtures thereof may also be used.

Any solvent to reactant ratio may be used to carry out step (a) of the process of the invention. The preferred range of the solvent to reactant ratio is from about 0.33:1 to about 10:1. Most preferably, the ratio is 2:1.

The preferred temperature for carrying out the monoaddition reaction of step (a) is in the range of from about 80° C. to about 150° C. At temperatures lower than 80° C., the reaction proceeds at a very slow rate. At temperatures higher than 150° C., side reactions, including decomposition of the solvent and TMI reactant, may become significant. A temperature in the range of 100° C. to 120° C. is most convenient to prepare the 1:1 adduct.

The preferred time for carrying out the monoaddition reaction of step (a) is in the range of from about 12 minutes to about 28 hours.

After the monoaddition reaction of step (a), the 1:1 adduct is isolated by cooling the reaction mixture and filtering the precipitated product. The product may be further purified by washing with an organic solvent capable of dissolving the solvent used in the process of the invention. An example of a solvent usable for this purpose is tetrahydrofuran.

In step (b) of the process, the adduct is hydroxymethylated (or methylolated) with 1 to 20 moles of formaldehyde per mole of the adduct, typically in water or an alcohol, or in a mixture of water and an alcohol such as normal butanol (n-butanol).

In step (c), the hydroxy groups in the methylolated 1:1 adduct are etherified with an alcohol under acidic conditions, typically at a pH range from 0.5 to 6.0, and preferably from about 2 to 4. The alcohol used to etherify the methylolated 1:1 adduct is usually used in a large excess to ensure a high degree of etherification and to prevent self-crosslinking of the product. Therefore, the alcohol used for etherification typically is the reaction solvent.

When mixed alkoxymethylated aminoplasts are desirable, a mixture of alcohols may be used both as reactant and as solvent.

Curable Composition

The novel aminoplasts of the invention may be used as crosslinking agents in curable compositions to produce, upon curing, crosslinked films or objects useful in coatings, adhesives, conventional moldings, reactive injection moldings, composites, laminates, binders, and others.

The curable composition comprises:

(i) an aminoplast crosslinking agent represented by the formula:

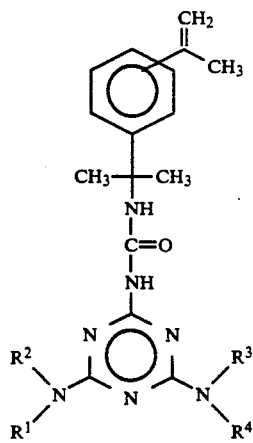

wherein the point of attachment of the isopropenyl group is meta-, or para-, or a mixture thereof, and wherein each of $R^1$, $R^2$, $R^3$, and $R^4$ is independently selected from the group consisting of hydrogen, hydroxymethyl, an alkoxymethyl of 1 to 6 carbon atoms, an aminoplast-containing group derived from condensation thereof, and mixtures of any of the preceding groups with the proviso that at least one of the $R^1$, $R^2$, $R^3$, and $R^3$ groups are independently selected from the group consisting of hydroxymethyl, an alkoxymethyl of 1 to 6 carbon atoms, and mixtures thereof; and (ii) a polyfunctional active hydrogen-containing material.

Aminoplast Crosslinking Agents

The aminoplast crosslinking agents usable in the curable compositions are the novel aminoplasts of the invention having at least two crosslinkably reactive functions at least one of which is selected from the group consisting of hydroxymethyl, alkoxymethyl, and a mixture thereof.

Polyfunctional Materials

The polyfunctional materials usable in the invention are polyfunctional active hydrogen-containing materials.

Suitable polyfunctional materials may be polymercaptans, polycarboxylic acids, polyamides, epoxy or urethane prepolymers, alkyds, and polyols such as acrylic resins containing pendant or terminal hydroxyl functionalities, polyester resins with pendant or terminal hydroxyl functionalities and polyhydric alcohols. These are described in greater detail below.

The polyfunctional materials and resins used in the compositions of the invention preferably have a molecular weight of from about 60 to about 50,000 and comprise at least one class of an active hydrogen functionality selected from the group consisting of hydroxy, carboxy, amido, mercapto, and a group convertible thereto.

The hydroxyfunctional polyfunctional materials used in formulating the curable compositions of this invention preferably are resins that have molecular weights in the range of from about 500 to about 50,000, and hydroxyl group equivalent weights of from about 200 to about 4,000.

An example of a suitable polyfunctional polyester resin usable in the curable compositions of this invention is OXYESTER ® Z 1439 Branched Polyester Resin, a product of Chemische Werke Hüls AG, Germany having the following physical and chemical properties:

| | |
|---|---|
| Hydroxyl Content (% by weight) | 2 |
| Hydroxyl Number | 65 |
| Equivalent Weight | 863 |
| Solids Content (% by weight) | 50 |

Another example of a suitable polyfunctional polyester resin particularly suited for use in coil coatings is CYPLEX ® 1531 modified Polyester Resin, a product of American Cyanamid Company, Wayne, N.J., having the following physical and chemical properties:

| | |
|---|---|
| Solids | |
| (Weight %) | 60 |
| (Volume %) | 52.9 |
| Color (Gardner 1963) | 6 (max.) |
| Viscosity (Gardner-Holt, 25° C.) | Y-$Z_2$ |
| Hydroxyl Number (solids) | 30 |
| Equivalent Weight (solids) | 1,870 |
| Molecular Weight, approximate | 4,000 |
| Acid number (solids) | 10 (max.) |
| Solvesso 150 Aromatic Hydrocarbon Solvent (%) (a product of Humble Oil and Refining Company) | 40 |

Another example of a suitable polyfunctional resin for coil coating is CYPLEX ® 1538 Modified Polyester Resin, a product of American Cyanamid Company, Wayne, N.J., having the following properties:

| | |
|---|---|
| Solids | |
| (Weight %) | 65 |
| (Volume) | 58 |
| Color (Gardner 1963) | 6 (max.) |
| Viscosity (Gardner-Holt, 25° C.) | $Z_1$-$Z_3$ |
| Hydroxyl Number (Solids) | 40 |
| Equivalent Weight (Solids) | 1400 |
| Molecular Weight, approximate | 2800 |
| Acid Number (Solids) | 10 (max.) |
| Solvesso 150 Aromatic Hydrocarbon Solvent (%) | 35 |

Another example of a suitable polyfunctional resin particularly suited to coil coatings is CYPLEX ® 1546 Oil-Free Polyester Resin, a product of American Cyanamid Company, Wayne, N.J., having the following properties:

| | |
|---|---|
| Non-Volatiles (Weight %) | 70 ± 2 |
| Color (Gardner 1963, max.) | 4 |
| Viscosity (Gardner-Holt, 25° C.) | $Z_1$-$Z_3$ |
| Acid Number (resin solids, max) | 10 |
| Hydroxyl Number (resin solids) | 35-40 |
| Equivalent weight | 1,400-1,600 |

An example of a suitable acrylic resin for non-coil coating applications is JONCRYL ® 500 Acrylic Resin, a product of S.C. Johnson and Son, Inc., Racine, Wis., having the following properties:

| | |
|---|---|
| Solids Content (Weight %) | 80 |
| Viscosity at Room Temperature (Centipoise) | 4,000 |
| Hydroxyl Number (based on solids) | 140 |
| Equivalent Weight (based on solids) | 400 |

| | |
|---|---|
| Molecular Weight (Mn)* | 1,300 |
| Polydispersity (Mw/Mn)** | 1.7 |

*Mn = Number Average Molecular Weight
**Mw = Weight Average Molecular Weight

ARAKOTE® 3109 Hydroxy-Terminated Polyester Resin, a product of Ciba-Geigy Corporation, Hawthorne, N.Y., is an example of a solid polyester resin particularly suitable to powder coating, and has the following physical and chemical properties:

| | |
|---|---|
| Hydroxyl Number | 27–32 |
| Equivalent Weight | 1,900 |
| Tg (Glass Transition, °C.) | 66 |
| ICI Viscosity at 200° C. (Poise) | 40 |
| Appearance | Colorless Solid |

JONCRYL® SCX-800 A Acrylic Resin and JONCRYLO SCX-800 B Acrylic Resin, products of S.C. Johnson and Son, Inc., examples of solid acrylic resins, also are suitable for powder coatings, and have the following physical and chemical properties:

| | SCX-800A | SCX-800B |
|---|---|---|
| Non-Volatiles (Weight %) | 98 | 97 |
| Hydroxyl Number | 43 | 40 |
| Equivalent Weight | 1300 | 1402 |
| Acid Value (mg KOH/g) | 15 | 15–20 |
| Tg (Glass Transition, °C.) | 43 | 43 |
| Softening Point (°C.) | 100 | 107 |
| ICI Viscosity at 200° C.(Poise) | 25 | 45–50 |

In addition to the examples cited above, a variety of commercial polyester resins may be used as the polyfunctional ingredient of the invention, provided such resins have suitable chemical and physical properties similar to those set forth above for ingredient (ii).

Optionally, the curable compositions of the invention may further comprise a cure catalyst to accelerate the curing process at a given temperature or to reduce the cure temperature at a given cure time.

The catalyst, if present, is typically an acid selected from the group consisting of sulfonic, carboxylic, phosphoric, sulfuric, and nitric acids. The preferred acid catalysts are sulfonic acids, including benzenesulfonic acid, para-toluenesulfonic acid, naphthalenesulfonic acid, dinonylnaphthalenesulfonic acid, dodecylbenzenesulfonic acid, methanesulfonic acid, and mixtures thereof.

Other Ingredients

The curable compositions of the invention may optionally contain a liquid medium, which liquid medium may be used to aid the uniform application and transport of the curable composition. Any or all of the ingredients of the composition may be contacted with the liquid medium. Moreover, the liquid medium may permit formation of a dispersion, suspension, emulsion, invert emulsion, or solution of the curable composition ingredients, including other optional ingredients.

Particularly preferred is a liquid medium which is a solvent or a diluent for the curable composition ingredients (i) and (ii). The preferred solvent or diluent is selected from the group consisting of water, alcohols, ketones, ethers, esters, aliphatic hydrocarbons, aromatic hydrocarbons, halogenated hydrocarbons, and mixtures thereof.

Other optional ingredients include fillers, pigments, flow control agents, anticratering additives, antioxidants, stabilizing alcohols, ultraviolet light stabilizers, plasticizers, pigment wetting additives, levelling additives, mar-proofers, mold release agents, and corrosion inhibitors.

Ratio Of The Ingredients

The weight ratio of the crosslinker (i) to polyfunctional material (ii) is from about 3:1 to about 1:40 and preferably 1:1 to 1:5. The weight percent of the crosslinker (i) in the curable composition is from about 2.5 to about 75.

The weight ratio of the catalyst, when present, to the crosslinker (i) in the curable composition is from about 1:4 to about 1:1,000 and the weight percent of catalyst in the curable composition is from about 0.01 to about 5.

The weight percent of the optional liquid medium ranges from zero to about 80 and the weight ratio of the liquid medium to the total weight of the ingredients (i) and (ii) of the composition ranges from about 0.001 to about 4.

Improved Method Of Coating

The curable compositions may be used in the improved method of the invention to prepare coatings such as solution coatings, emulsion coatings, powder coatings, coil coatings, electrodeposition coatings, and the like. They may also be used as laminating resins, adhesives or molding compounds.

This invention, therefore, is an improved method for coating of the type having the steps of (I) contacting a substrate with a curable composition containing a crosslinking agent and a polyfunctional active hydrogen-containing material, and (II) thereafter curing, wherein the improvement comprises:

(A) contacting said substrate with a curable composition comprising:
  (i) an aminoplast crosslinking agent represented by the formula:

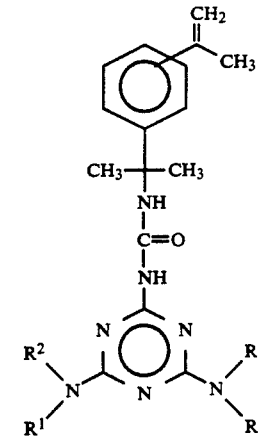

wherein the point of attachment of the isopropenyl group is meta- or para-, or a mixture thereof, and wherein each of $R^1$, $R^2$, $R^3$, and $R^4$ is independently selected from the group consisting of hydrogen, hydroxymethyl, an alkoxymethyl of 1 to 6 carbon atoms, an aminoplast-containing group derived from condensation thereof, and mixtures of any of the preceding groups, with the proviso that at least one of the R$^1$, R$^2$, R$^3$, and R$^4$ groups are independently selected from the group consisting of hydroxymethyl, alkoxymethyl of 1 to 6 carbon atoms, and mixtures thereof, and (ii) a polyfunctional active hydrogen-containing material, and (B) thereafter heat-curing said curable composition.

The curable compositions usable in the improved method are the novel curable compositions of the invention described hereinabove containing the novel aminoplast crosslinking agents of the invention having at least two crosslinkable reactive functions at least one of which is selected from the group consisting of hydroxymethyl, alkoxymethyl, and mixtures thereof.

The curable composition may be applied onto a substrate by spraying, padding, brushing, roller-coating, curtaincoating, flowcoating, electrocoating, dipping, or electrostatic spraying. The applied curable composition is thereafter cured, typically, at a temperature in the range of from about 80° C. to about 160° C. within a period of, typically, 5 minutes to 1 hour to produce crosslinked films or objects.

EXAMPLE 1

PREPARATION OF M-TMI/MELAMINE 1:1 ADDUCT

In a 2 liter three neck glass reactor equipped with agitator, thermometer, reflux condenser, nitrogen inlet and dropping funnel, 252 g (2 moles) of melamine was dispersed in 800 ml of DMSO (Dimethylsulfoxide) under vigorous agitation. A solution of 423 g (2.1 moles) of M-TMI in 200 ml DMSO was added to the slurry at 110°-113° C. in 3.5 hours. The reaction temperature was maintained for an additional hour. To maintain efficient agitation, the thickening slurry was diluted several times during the reaction with a total of 150 ml of DMSO. After cooling to ambient temperature, the reaction mixture was filtered, the white solid was rinsed on a filter with THF (tetrahydrofuran) and reslurried in 800 ml of THF. After agitation at 64° C. for 80 minutes, the product was filtered, rinsed on the filter with THF and dried first in a hot air circulation oven at 60° C. overnight (16 hours), then in a vacuum oven (full pump vacuum) at 90°-100° C. for 4 hours. The yield of the white solid product was 665 g. From the first filtrate 85 g and from the second (wash) 73 g of white solids were recovered. Infrared (IR) and Thermal Gravimetric Analysis (TGA) indicated that these products still contained 15-20% of DMSO.

The main product was characterized by NMR (Nuclear Magnetic Resonance), IR and thermal analysis. It is practically insoluble in most organic solvents, sparingly soluble in aprotic solvents such as DMSO, N-methyl-pyrrolidone, DMF (dimethylformamide), etc. Both carbon and proton NMR, as well as the IR spectra were consistent with a 1:1 adduct structure. TGA indicated about a 20% weight loss in the range of 100°-125° C. (DMSO). Major weight loss is observed above 245° C. Major thermal event by DSC (differential scanning calorimetry) is an endotherm occurring in the temperature range in which the major weight loss is observed by TGA (extras. onset: 223° C.). Liquidification is observed by TM (Thermal Microscopy) in the same range (onset 232° C.) and "boiling" started at 248° C.

EXAMPLE 2

PREPARATION OF MIXED ALKOXYMETHYLATED MONOMERIC AMINOPLAST CROSSLINKING AGENT

A suitable reactor equipped with stirrer, reflux condenser and thermometer was charged with 120 g of butyl formcel. (Butyl formcel comprises formaldehyde (40%), normal butanol (53%), and water (7%) by weight.) and the pH adjusted with 20% caustic solution to 10.1. Then 80 g of the product of Example 1 was added and the temperature of the slurry raised to 85° C.; after eight minutes a clear solution was formed. The temperature was maintained at 85°-90° C. for an additional 30 minutes, then 84 g of n-butanol was added. At 65° C., the pH was adjusted to 2.5 by addition of 0.5 ml of 70% nitric acid and the temperature was maintained for 20 minutes. During the following 35 minutes, 55 ml of distillate was removed at 65°-68° C. and 200 Mm Hg (about 27 kilo Pascals). The distillate was replaced by adding portionwise to the reactor the same amount of n-butanol. The reaction mixture was cooled to 35° C. and 1.25 ml 20% caustic was added to adjust the pH to 9.6. The volatiles were stripped to 96° C./100 Mm Hg (about 13 kilo pascals) and 115 g of distillate was collected. At 55° C.P 96 g of methanol was charged followed by 0.5 ml of 70% nitric acid at 40° C. (PH=2.1), and the temperature was maintained at 40°-43° C. for 40 minutes. After adjusting the pH to 9.5 with 1.2 ml of 20% caustic solution, 112 g distillate was removed at 90 mm Hg (12 kilo pascals) up to 95° C. The 120 g of the colorless, moderately viscous resin obtained was diluted with 17 g of toluene and filtered at 80° C. under approximately 2,000 mm Hg pressure of nitrogen gas (about 276 kilo pascals), to give a clear, colorless resin, the novel crosslinking agent of the invention, having the following characteristics:

| | | |
|---|---|---|
| HPSEC: | 81.7% | Monomer (High Performance Size Exclusion Chromatography Areas) |
| | 14.8% | Dimer (Areas) |
| | 3.5% | Trimer (Areas) |
| NMR: | CH$_3$/CH$_2$ = | 0.22 (ratio) |
| | nBu/CH$_2$ = | 0.67 (ratio) |
| | CH$_2$/Adduct = | 3.3 (ratio) |
| FREE CH$_2$O: | 0.55% (by weight) | |
| METHYLOL: | 2.48% (by weight) | |
| SOLIDS: | Pan = 89.2% (by weight) | |
| | Foil = 95.2% (by weight) | |
| CH$_2$O/ADDUCT: | 3.12 (Based on bound formaldehyde and nitrogen analysis) | |

EXAMPLE 3

The procedure of Example 2 was repeated with the exception that methyl formcel (methyl formcel comprises formaldehyde (55%), methanol (35%) and water (10%) by weight) was used instead of butyl formcel, and the n-butanol was replaced with methanol. The product was a methoxymethylated analog of the product of Example 2. The methoxymethylated product is another example of the crosslinking agents of the invention and has the following characteristics:

| | | |
|---|---|---|
| NMR: | CH$_3$/CH$_2$ = | 0.96 (ratio) |

| | -continued | |
|---|---|---|
| FREE | CH₂O/Adduct = | 1.7 |
| | CH₂O = | 0.97% (by weight) |
| | CH₂OH = | 1.93% (by weight) |
| RESIDUAL DMSO = | | 3% (by weight) |
| HPSEC: | 73.3% | Monomer (High Performance Size Exclusion Chromatography Areas) |
| | 16.3% | Dimer (Areas) |
| | 2.9% | Trimer (Areas) |
| | 6.9% | Higher Oligomers (Areas) |
| FOIL SOLIDS: | | 84.5% (by weight, the balance being ethanol) |
| SOLUBILITY: | | Soluble in xylene at 70° C. and in normal butanol at 60° C. A precipitate forms from the n-butanol solution at room temperature on standing. |

EXAMPLE 4

The crosslinking agents of Example 2 and Example 3 and JONCRYL ® 500 resin, a product of S. C. Johnson and Son, Inc., Racine, Wis., were cured. The physical properties of the cured films were compared with cured films obtained by using CYMEL ® 303 and CYMEL ® 1168 crosslinking agents, both products of American Cyanamid Company, Wayne, N.J. CYMEL ® 303 crosslinker is a substantially fully methoxymethylated melamine. CYMEL ® 1168 crosslinker is a substantially fully mixed methoxymethylated and isobutoxymethylated melamine. The film properties are summarized in Table 1. The formulations were as follows:

Weight ratio of JONCRYL ® 500 Resin/CROSSLINKER: 65/35

Weight percent of para-toluenesulfonic acid (on binder solids): 0.3

Substrate: Electrocoated cold roll steel Film Thickness: 1.6–1.8 mils (0.041–0.046 mm)

TABLE 1
FILM PROPERTIES OF COATINGS PREPARED FROM THE NOVEL AMINOPLAST CROSSLINKING AGENTS OF EXAMPLE 2 AND EXAMPLE 3 WITH JONCRYL ® 500 RESIN IN CLEAR COATS: A COMPARISON WITH CYMEL ® 300 AND CYMEL ® 1168 CROSSLINKING AGENTS USED TO PREPARE THE CLEAR COAT

| | CYMEL ® 303 | CYMEL ® 1168 | EXAMPLE 2 | EXAMPLE 3 |
|---|---|---|---|---|
| 121° C./30 MIN. CURE | | | | |
| TUKON HARDNESS (ASTM D-1474-85) | 10.1 | 7.4 | 9.6 | 10.9 |
| MEK DOUBLE RUBS | | | | |
| TO MAR | 200+ | 200+ | 200+ | 10 |
| TO REMOVE | 200+ | 200+ | 200+ | 200* |
| 149° C./30 MIN. CURE | | | | |
| TUKON HARDNESS (ASTM D-1474-85) | 11.5 | 8.9 | 10.9 | 12.4 |
| MEK DOUBLE RUBS | | | | |
| TO MAR | 200+ | 200+ | 200+ | 50 |
| TO REMOVE | 200+ | 200+ | 200+ | 200+ |

*Film easily scratches off after 200 MEK double rubs.

EXAMPLE 5

The procedure of Example 4 was used to prepare four additional cured films (clear coats) with the exception that both cure catalyst concentration and the JONCRYL ® 500 to crosslinker ratios were modified as shown in Table 2. After curing, environmental etch and acid spot tests were carried out.

In the acid spot tests, the cured films are contacted with an acid. After exposure to 38% sulfuric acid at room temperature overnight, no evidence of an acid spot could be detected on films prepared from JONCRYL ® 500 and the crosslinker of the invention (Example 2), whereas the film prepared using CYMEL ® 1168 had a notable, but slight, haze.

The results of the environmental etch test are summarized in Table 2.

TABLE 2
RESISTANCE PROPERTIES OF THE NOVEL AMINOPLAST CROSSLINKING AGENTS OF EXAMPLE 2 WITH JONCRYL ® 500 RESIN IN CLEAR COATS: A COMPARISON WITH CYMEL ® 1168 CROSSLINKERS

| CROSSLINKERS | JONCRYL*500/ CROSSLINKER (RATIO) | CURE CATALYST (para-Toluenesulfonic Acid) (WT. %) | ATTACK RATING* | | |
|---|---|---|---|---|---|
| | | | H₂SO₄ (50 ppm) | HNO₃ (15 ppm) | H₂SO₄ + HNO₃ (20 + 20 ppm) |
| Example 2 | 65/35 | 0.3 | 5 | 3 | 3 |
| Example 2 | 50/50 | 0.3 | 5 | 1 | 2 |
| Example 2 | 50/50 | 1.0 | 5 | 0 | 1 |
| CYMEL*1168 | 65/35 | 0.3 | 5 | 3 | 3 |

*Attach rating on a scale of 0 to 5.
5 = Greatest Attack
0 = No Visible Attack

EXAMPLE 6

The procedure of Example 2 is again followed except that 200.0 g of butyl formcel are employed such as to react all the NH sites of the metanine moiety. Coatings produced from the resultant aminoplast show excellent properties.

Although the present invention has been described with reference to certain preferred embodiments, it is apparent that modifications and variations thereof may be made by those skilled in the art without departing from the scope of this invention as defined by the appended claims.

We claim:

1. A composition of matter represented by the formula:

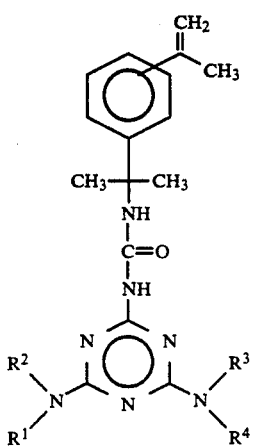

wherein the point of attachment of the isopropenyl group is meta-, para-, or a mixture thereof, and wherein each of $R^1$, $R^2$, $R^3$, and $R^4$ is independently selected from the group consisting of hydrogen, hydroxymethyl, an alkoxymethyl, an aminoplast-containing group derived from condensation thereof, and mixtures of any of the preceding moieties.

2. The composition of matter of claim 1 represented by the formula:

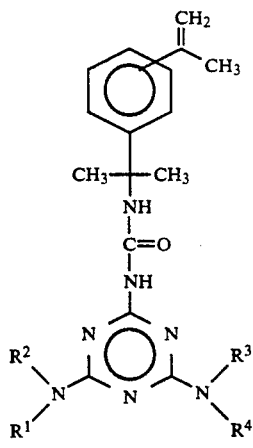

wherein each of $R^1$, $R^2$, $R^3$, and $R^4$ independently selected from the group consisting of hydrogen, hydroxymethyl, an alkoxymethyl of 1 to 6 carbon atoms, an aminoplast-containing group derived from condensation thereof, and mixtures of any of the preceding moieties.

3. The composition of matter of claim 2 wherein at least one of the $R^1$, $R^2$, $R^3$, and $R^4$ moieties are independently selected from the group consisting of hydroxymethyl, an alkoxymethyl of 1 to 6 carbon atoms, and mixtures thereof.

4. The composition of matter of claim 1 represented by the formula:

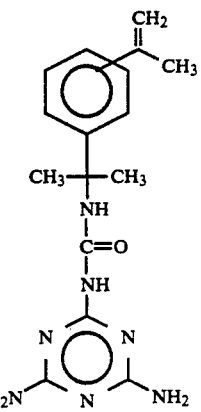

5. The composition of matter of claim 1 represented by the formula:

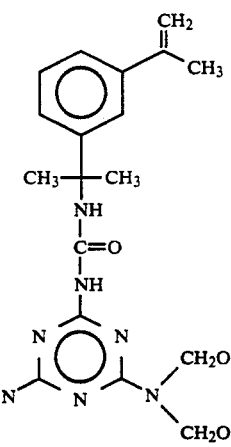

wherein each of $R^5$, $R^6$, $R^7$, and $R^8$ is independently selected from the group consisting of hydrogen, methyl, ethyl, 1-propyl, 2-propyl, 1-butyl, 2-butyl, iso-butyl, 1-pentyl, 1-hexyl, and cyclohexyl moieties, and 6. The composition of claim 5 wherein $R^5$, $R^6$, $R^7$ & $R^8$ are all hydrogen.

7. The composition of matter of claim 1 represented by the formula:

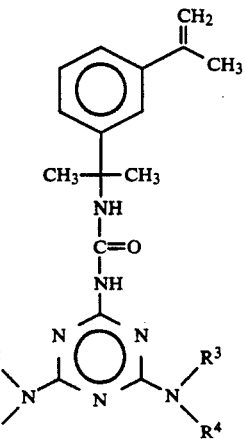

wherein each of $R^1$, $R^2$, $R^3$, and $R^4$ is independently selected from the group consisting of hydrogen, hydroxymethyl, an alkoxymethyl of 1 to 6 carbon atoms, an aminoplast-containing group derived from condensation thereof, and mixtures of any of the preceding moieties.

8. A process for preparing an alkoxymethylated aminoplast comprising:
(a) contacting melamine with isopropenyl-alpha, alpha-dimethylbenzyl isocyanate in a solvent having a high dielectric constant at a temperature and for a length of time sufficient to produce a 1:1 adduct,
(b) contacting the adduct of step (a) with 2 to moles of formaldehyde per mole of adduct to produce a hydroxymethylated adduct, and
(c) contacting said hydroxymethylated adduct of step (b) with 2 to 30 moles of an alcohol per mole of hydroxymethylated adduct at an acidic pH to produce an alkoxymethylated aminoplast.

9. The process of claim 8 wherein the isopropenyl-alpha, alpha-dimethylbenzyl isocyanate in step (a) is selected from the group consisting of meta-isopropenylalpha, alpha-dimethylbenzyl isocyanate; para-isopropenyl-alpha, alpha-dimethylbenzyl isocyanate; and a mixture thereof.

10. The process of claim 8 wherein the ratio of isopropenyl-alpha, alpha-dimethylbenzyl isocyanate to melamine in step (a) is from about 0.5:1 to about 5:1.

11. The process of claim 8 wherein the ratio of the solvent to the reactants in step (a) is in the range of from about 0.33:1 to about 10:1.

12. The process of claim 11 wherein the ratio is about 2:1.

13. The process of claim 8 wherein the temperature in step (a) is in the range of from about 80° C. to about 150° C.

14. The process of claim 8 wherein the time in step (a) is in the range of from about 12 minutes to about 28 hours.

15. The process of claim 8 wherein the 1:1 adduct of step (a) is isolated by filtration.

16. The process of claim 8 wherein contacting of the adduct with formaldehyde in step (b) is carried out in a solvent selected from the group consisting of an alcohol, water, and a mixture thereof.

17. The process of claim 16 wherein the alcohol in step (b) is normal butanol or methanol.

18. The process of claim 8 wherein the alcohol in step (c) is methanol, normal butanol, or a mixture 19. The process of claim 8 wherein the pH in step (c) is in the range of from about 0.5 to 6, and preferably 20. A curable composition comprising:
(i) an aminoplast crosslinking agent represented by the formula:

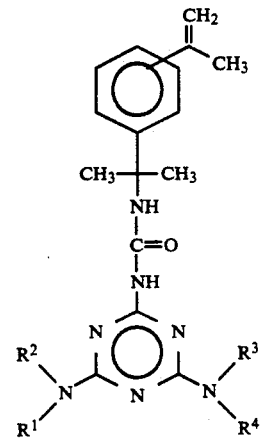

wherein the point of attachment of the isopropenyl group is meta-, para-, or a mixture thereof, and wherein each of $R^1$, $R^2$, $R^3$, and $R^4$ is independently selected from the group consisting of hydrogen, hydroxymethyl, an alkoxymethyl of 1 to 6 carbon atoms, an aminoplast-containing group derived from condensation thereof and mixtures of any of the preceding moieties, with the proviso that at least one of $R^1$, $R^2$, $R^3$, and $R^4$ are independently selected from the group consisting of hydroxymethyl, an alkoxymethyl of 1 to 6 carbon atoms, and mixtures thereof, and
(ii) a polyfunctional active hydrogen-containing material.

21. The curable composition of claim 20 wherein the aminoplast crosslinking agent (i) is represented by the formula:

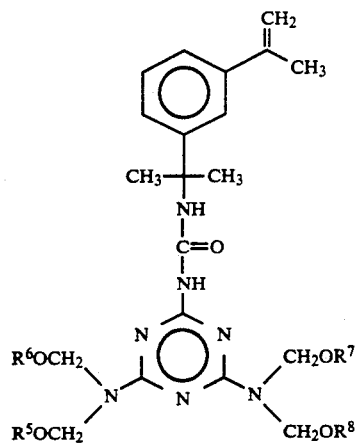

wherein each of $R^5$, $R^6$, $R^7$, and $R^8$ is independently selected from the group consisting of hydrogen, methyl, ethyl, 1-propyl, 2-propyl, 1-butyl, 2-butyl, isobutyl, 1-pentyl, 1-hexyl, and cyclohexyl moieties, andmixtures thereof.

22. The curable composition of claim 20 wherein the aminoplast crosslinking agent (i) comprises a mixed alkoxymethylated aminoplast represented by the formula:

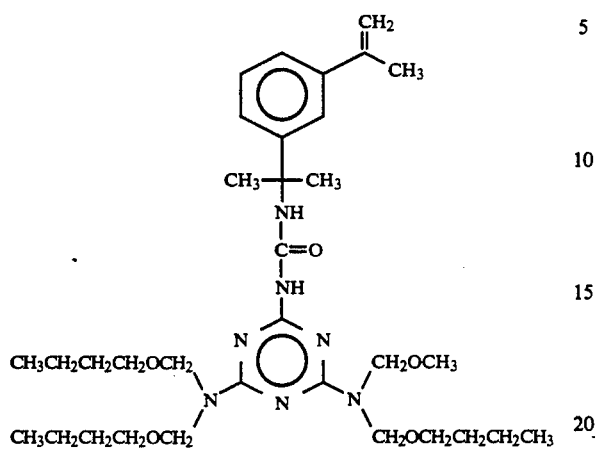

23. The curable composition of claim 20 wherein the polyfunctional active hydrogen-containing material (ii) comprises at least one class of an active hydrogen functionality selected from the group consisting of hydroxy, carboxy, amido, mercapto, and a group convertible thereto.

24. The curable composition of claim 23 wherein the, polyfunctional active hydrogen-containing material (ii) comprises hydroxyfunctional compounds and resins selected front the group consisting of polyhydric alcohols, polyesters, polyurethanes, acrylics, products of condensation of epoxy resins, and mixtures thereof.

25. The curable composition of claim 25 further comprising, from about 0.01 to about 5.0 weight percent, a cure catalyst.

26. The curable composition of claim 25 wherein the cure catalyst is an acid selected from the group consisting of sulfonic, carboxylic, phosphoric, sulfuric, nitric, and mixtures thereof.

27. The curable composition of claim 26 wherein the cure catalyst is a sulfonic acid selected from the group consisting of benzenesulfonic acid, paratoluenesulfonic acid, napthalenesulfonic acid, dinonylnaphthalenedisulfonic acid, dodecylbenzenesulfonic acid, methanesulfonic acid, and mixtures thereof.

28. The curable composition of claim 20 wherein the ratio of the aminoplast crosslinking agent (i) to the polyfunctional active hydrogen-containing material (ii) is from about 3:1 to about 1:40.

29. The curable composition of claim 28 wherein the ratio is 1:1 to 1:5.

30. An improved method for coating of the type having the steps of (I) contacting a substrate with a curable composition containing a crosslinking agent and a polyfunctional active hydrogen-containing material, and (II) thereafter curing, wherein the improvement comprises:

(A) contacting said substrate with a curable composition comprising:

(i) an aminoplast crosslinking agent represented by the formula:

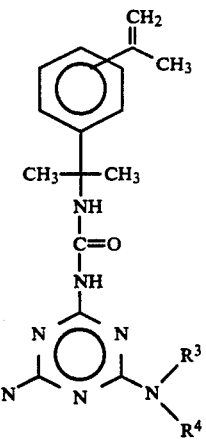

wherein the point of attachment of the isopropenyl group is meta-, para-, or a mixture thereof, and wherein each of $R^1$, $R^2$, $R^3$, and $R^4$ is independently selected from the group consisting of hydrogen, hydroxymethyl, an alkoxymethyl of 1 to 6 carbon atoms, an aminoplast-containing group derived from condensation thereof, and mixtures of any of the preceding, with the proviso that at least one of $R^1$, $R^2$, $R^3$, and $R^4$ are independently selected from the group consisting of hydroxymethyl, an alkoxymethyl of 1 to 6 carbon atoms, and mixtures thereof, and (ii) a polyfunctional active hydrogen-containing material; and (B) thereafter heat curing said curable composition.

31. The method of claim 30 wherein the aminoplast crosslinking agent (i) is represented by the formula of claim 30, wherein each of $R^5$, $R^6$, $R^7$, and $R^8$ is independently selected from the group consisting of hydrogen, methyl, ethyl, 1-propyl, 2-propyl, 1-butyl, 2-butyl, isobutyl, 1-pentyl, 1-hexyl, cyclohexyl moieties, and mixtures thereof.

32. The method of claim 30 wherein the aminoplast crosslinking agent (i) comprises a mixed alkoxymethylated aminoplast represented by the formula:

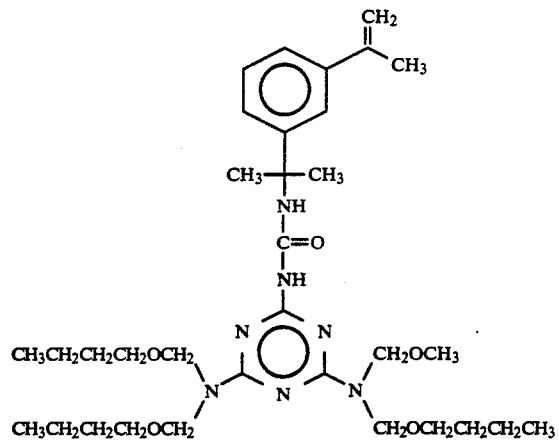

33. The method of claim 30 wherein the polyfunctional active hydrogen-containing material (ii) comprises at least one class of active hydrogen functionality selected from the group consisting of hydroxy, carboxy, amido, mercapto, and a group convertible thereto.

34. The method of claim 30 wherein the curable composition further comprises an acid cure catalyst.

35. The method of claim 30 wherein the curing is carried out at a temperature in the range of from about 80° C. to about 160° C.

36. A crosslinked film or object prepared by the method of claim 30.

* * * * *